(12) United States Patent
Masson et al.

(10) Patent No.: US 9,504,507 B2
(45) Date of Patent: Nov. 29, 2016

(54) INJECTOR DEVICE FOR INTRODUCING BIOCOMPATIBLE MATERIAL INTO DEEP ANATOMICAL AREAS

(71) Applicant: Tecres, S.p.A, Sommacampagna (IT)

(72) Inventors: Robert Masson, Windermere, FL (US); Renzo Soffiatti, Nogara (IT); Giovanni Faccioli, Monzambano (IT)

(73) Assignee: TECRES S.P.A., Sommacampagna (VR) (IT)

( * ) Notice: Subject to any disclaimer, the term of this patent is extended or adjusted under 35 U.S.C. 154(b) by 204 days.

(21) Appl. No.: 13/935,808

(22) Filed: Jul. 5, 2013

(65) Prior Publication Data

US 2015/0011946 A1  Jan. 8, 2015

(51) Int. Cl.
*A61B 17/88* (2006.01)
*A61M 5/31* (2006.01)
*A61M 5/315* (2006.01)

(52) U.S. Cl.
CPC ....... *A61B 17/8811* (2013.01); *A61B 17/8805* (2013.01); *A61M 5/3137* (2013.01); *A61M 5/31511* (2013.01); *A61M 2205/0216* (2013.01)

(58) Field of Classification Search
CPC .............. A61B 17/88; A61B 17/8802; A61B 17/8805; A61B 17/8811; A61B 17/8816; A61B 17/8819; A61B 17/8822; A61F 2/4601
USPC ..................................................... 606/92–94
See application file for complete search history.

(56) References Cited

U.S. PATENT DOCUMENTS

| | | | | |
|---|---|---|---|---|
| 1,325,699 A * | 12/1919 | Oesterhaus | ........... | A61M 31/00 604/218 |
| 3,757,781 A * | 9/1973 | Smart | ............... | A61M 37/0069 604/218 |
| 4,466,435 A * | 8/1984 | Murray | .............. | A61B 17/8808 141/189 |
| 4,625,722 A * | 12/1986 | Murray | ............. | A61B 17/8808 606/94 |
| 4,801,263 A * | 1/1989 | Clark | ..................... | A61C 5/062 433/90 |
| 5,092,854 A * | 3/1992 | Black | ................... | A61M 3/0279 604/243 |
| 5,954,728 A * | 9/1999 | Heller | ................. | A61B 17/8808 606/86 R |
| 6,048,346 A * | 4/2000 | Reiley et al. | ................... | 606/92 |
| 6,261,094 B1 * | 7/2001 | Dragan | .................. | A61C 5/066 433/90 |
| 6,379,152 B1 * | 4/2002 | Dragan | .................. | A61C 5/066 433/90 |
| 7,022,112 B2 * | 4/2006 | Pokorney | ........... | A61M 5/31511 604/227 |
| 7,118,378 B1 * | 10/2006 | Karapetyan | ..................... | 433/90 |
| 7,169,180 B2 * | 1/2007 | Brennan | ................... | A61F 2/12 128/898 |
| 2002/0049448 A1 * | 4/2002 | Sand et al. | ....................... | 606/92 |
| 2002/0058946 A1 * | 5/2002 | Gross | .............................. | 606/93 |

(Continued)

*Primary Examiner* — Christian Sevilla
*Assistant Examiner* — Eric S Gibson
(74) *Attorney, Agent, or Firm* — Tutunjian & Bitetto, P.C.

(57) ABSTRACT

Injector device for introducing biocompatible material into deep anatomical areas, positioned at the spine, the pelvis, the rachis and other similar locations, including a cannulated body and a piston for delivering the biological material equipped with a shaft, in which the cannulated body has a distal end, facing towards a user, and a proximal end, facing towards the anatomical area, in which the cannulated body includes a rectilinear section, equipped with a longitudinal axis, an inner lumen, in which the proximal end comprises an extrusion mouth of the biological material, in which the cannulated body also includes an end section that is curved and/or bent at the proximal end and in which the cannulated body is integral and rigid.

17 Claims, 3 Drawing Sheets

(56) References Cited

U.S. PATENT DOCUMENTS

| | | | |
|---|---|---|---|
| 2003/0105468 A1* | 6/2003 | Gorek | 606/92 |
| 2005/0216018 A1* | 9/2005 | Sennett | 606/79 |
| 2006/0122624 A1* | 6/2006 | Truckai et al. | 606/94 |
| 2006/0264964 A1* | 11/2006 | Scifert et al. | 606/92 |
| 2007/0027230 A1* | 2/2007 | Beyar et al. | 523/117 |
| 2007/0093759 A1* | 4/2007 | Sickler | 604/181 |
| 2007/0123983 A1* | 5/2007 | Brennan | A61F 2/12 623/8 |
| 2007/0185495 A1* | 8/2007 | Hess et al. | 606/93 |
| 2007/0197971 A1* | 8/2007 | Krueger et al. | 604/164.01 |
| 2007/0198024 A1* | 8/2007 | Plishka et al. | 606/93 |
| 2007/0233146 A1* | 10/2007 | Henniges et al. | 606/91 |
| 2008/0021463 A1* | 1/2008 | Georgy | 606/61 |
| 2008/0172060 A1* | 7/2008 | Collins | A61B 17/8811 606/94 |
| 2009/0281548 A1* | 11/2009 | Faccioli | 606/93 |
| 2009/0299282 A1* | 12/2009 | Lau et al. | 604/99.01 |
| 2009/0318925 A1* | 12/2009 | Campion et al. | 606/93 |
| 2010/0023017 A1* | 1/2010 | Beyar et al. | 606/94 |
| 2010/0298832 A1* | 11/2010 | Lau et al. | 606/80 |
| 2011/0004308 A1* | 1/2011 | Marino et al. | 623/17.12 |
| 2011/0196379 A1* | 8/2011 | Blakemore et al. | 606/93 |
| 2011/0306983 A1* | 12/2011 | O'Halloran et al. | 606/94 |
| 2012/0083790 A1* | 4/2012 | Dubach | 606/94 |
| 2012/0239050 A1* | 9/2012 | Linderman et al. | 606/94 |
| 2013/0144300 A1* | 6/2013 | Vogt et al. | 606/94 |
| 2014/0046245 A1* | 2/2014 | Cornacchia | 604/22 |
| 2014/0276581 A1* | 9/2014 | Lou et al. | 604/506 |
| 2014/0358188 A1* | 12/2014 | Larson et al. | 606/86 R |
| 2015/0011946 A1* | 1/2015 | Masson et al. | 604/218 |
| 2015/0045768 A1* | 2/2015 | Schmieding et al. | 604/506 |
| 2015/0105785 A1* | 4/2015 | Kapec et al. | 606/94 |

* cited by examiner

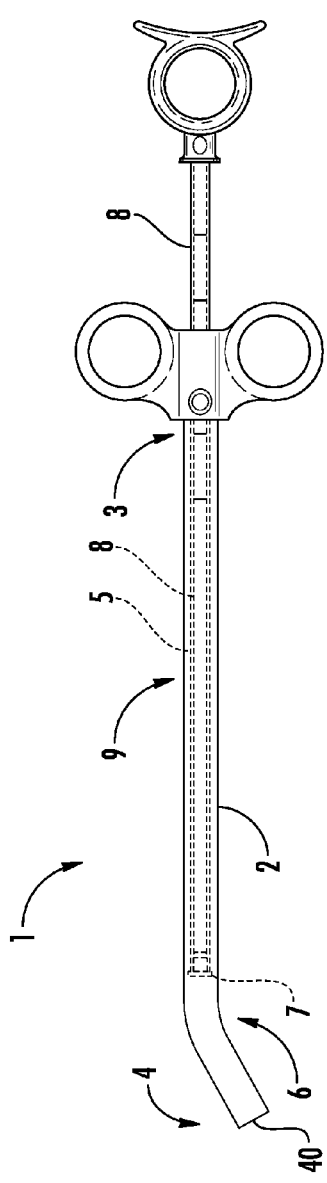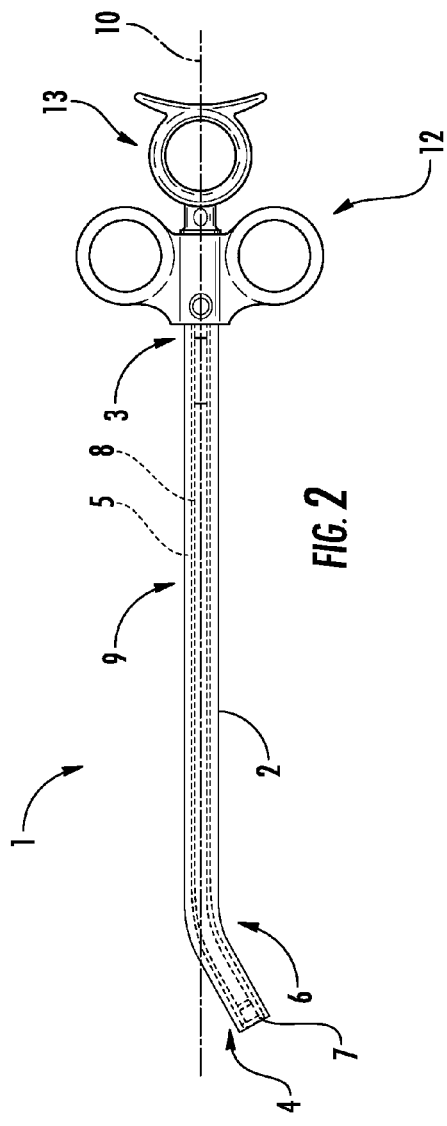

100
INJECTOR DEVICE FOR INTRODUCING BIOCOMPATIBLE MATERIAL INTO DEEP ANATOMICAL AREAS

TECHNICAL FIELD OF THE INVENTION

The present invention concerns an injector device for introducing biocompatible material into deep anatomical areas. In particular, the present invention concerns an injector device for introducing bone paste or other bone materials or bone cements at the spine, pelvis, rachis, etc. level.

DESCRIPTION OF RELATED ART

In the field of medicine, it is known to use injector devices for biocompatible or biological bone materials. In particular, on the market there are known injector devices that are able to reach deep or difficult locations, like for example spinal locations.

Access to such locations is particularly difficult both due to the depth to be reached and due to the risk of damaging the human body tissues adjacent to the injection site, during the insertion of such devices.

In greater detail, the injector devices conventionally used comprise a tubular duct made from elastically deformable material, capable of easily reaching the injection site, connected to a syringe or to another container filled with the material to be injected and equipped with a piston capable of generating a force that presses the material to be injected to cause it to be delivered into the site of interest.

Such devices are often connected to vacuum sources or to external devices capable of generating the force necessary to deliver even relatively fluid and viscous materials. However, known injector devices have the drawback of comprising numerous components, connected together, making the whole thing very complicated both in terms of their assembly and disassembly and their use.

Moreover, the containers of material are often disconnected from the actual injection cannulas, therefore requiring numerous connection and adaptation portions that must withstand the pressures, which may even be high, to which the material is subjected to cause it to be delivered.

SUMMARY OF THE INVENTION

The technical task of the present invention is therefore to devise an injector device for introducing biocompatible material into deep anatomical areas.

In such a technical task, a particular purpose of the present invention is to make an injector device that is simple to make and use and quick to use.

A further purpose of the present invention is to devise an injector device that is minimally invasive and that allows easy insertion inside deep anatomical locations. This task and these purposes are accomplished by the injector device for introducing biocompatible material into deep anatomical areas according to the attached claim 1. Further advantageous characteristics are described in the dependent claims.

BRIEF DESCRIPTION OF THE DRAWINGS

The characteristics of the invention will be better understood by any man skilled in the art from the following description and from the attached tables of drawings, given as a non-limiting example, in which:

FIG. 1 is a side view of the injector device for introducing biocompatible material into deep anatomical areas, according to the present invention, in which one of its components is illustrated in an intermediate position;

FIG. 2 is a side view of the injector device illustrated in FIG. 1, in which one of its components is illustrated in an end stop position;

DETAILED DESCRIPTION

Figure 3:
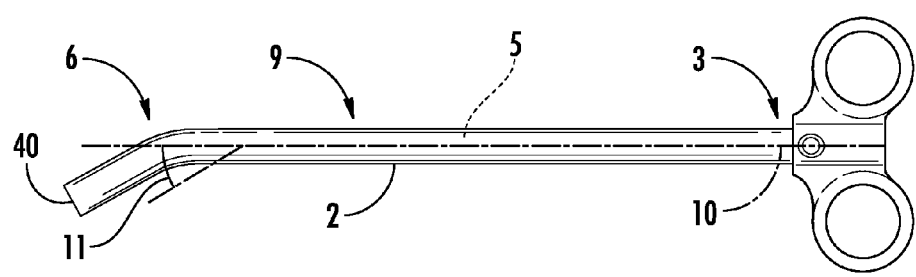
FIG. 3 is a side view of a component of the injector device illustrated in FIGS. 1 and 2.
Figure 4:
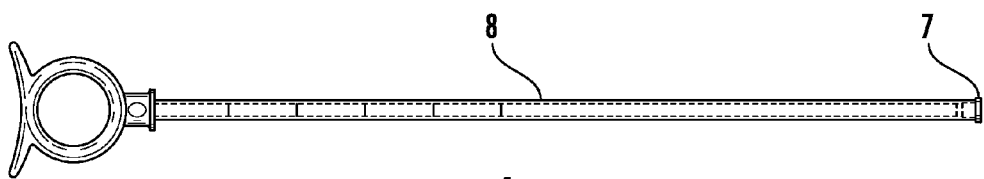
FIG. 4 is a side view of a further component of the injector device illustrated in FIGS. 1 and 2.

With reference to the attached FIG. 1, an injector device for introducing biocompatible material into deep anatomical areas, according to the present invention, is wholly indicated with 1.

In particular, the deep anatomical areas are at the spine, the pelvis, the rachis and at other similar locations. The biocompatible material injected through the device 1 comprises osteoinductive material, biological material, bone paste, bone material, bone substitute material, bone substitutes in general, demineralised bone matrix (DBM), mixtures thereof and similar materials suitable for the purpose. Such a biocompatible material can also comprise synthetic bone materials, synthetic biological adduct, bone cement, etc.

Such a biocompatible material has a pasty and/or gel-like consistency; the consistency of the biocompatible material is viscous.

Such a biocompatible material can contain particles or granules of demineralised bone or of synthetic granular material; such particles or granules have dimensions that can reach 15 mm in diameter; in a version of the invention, such particles or granules have dimensions comprised between 1 mm and 5 mm.

In particular, a surgical technique, in which the device according to the present invention is used, foresees to arrange the biocompatible, possibly osseoinductive, material between two adjacent vertebrae.

The injector device 1 has a syringe configuration that, due to its dimensions and its operation, satisfies the needs indicated above.

In particular, the injector device 1 comprises a cannulated body 2.

The cannulated body 2 has a distal end 3, facing towards the user, and a proximal end 4, facing towards the injection site.

The cannulated body 2 also has an inner lumen 5 and a tubular configuration having a main longitudinal axis 10.

In particular, the cannulated body 2 has a length such that the injector device 1 is suitable for passing through the soft tissues to reach the deep anatomical location at which the injection has to take place.

According to one operating technique, the injector device 1 is inserted through the same surgical tunnel made to remove the disc residues before the injection of the biocompatible material.

The length of the injector device 1 and of its cannulated body 2 is such as to allow the extrusion of the biocompatible material, in a controlled manner, from outside the body of the patient.

At the proximal end 4 the extrusion of the biocompatible material takes place. At the proximal end 4, therefore, there is an extrusion mouth 40 of the injector device 1.

The injector device 1 comprises a rectilinear section 9 and an end section 6 that is curved and/or bent. Such an end section 6 is foreseen at the proximal end 4 of the cannulated body 2 and/or of the injector device 1.

In particular, the end section 6 is positioned between the extrusion mouth 40 and the rectilinear section 9. The presence of the end section 6 that is curved and/or bent allows the orientation of the delivery and of the positioning of the biological material.

As illustrated in FIG. 3, the end section 6 has an angle of curvature 11, with respect to the main longitudinal axis 10 of the rectilinear section 9 of the cannulated body 2. The angle 11 is comprised between 15° and 45° or between 5° and 70° or between 0° and 90°. In a version of the invention, such an end section 6 has an inclination equal to an angle 11 of 30°.

The cannulated body 2 is integral, monolithic and a monoblock. Therefore, the rectilinear section 9, the end section 6 and the extrusion mouth 40 are made in a single continuous piece.

In this way, it is possible to avoid the presence of complicated and expensive connection means that, in the prior art, are used to connect the syringe means for expelling the material to cannulas of various materials and configurations that are used to reach the insertion site, which often has a deep or difficult-to-reach position.

Thanks to the present device, the delivery can take place, as explained in greater detail hereafter, by making all of the material contained in the device itself come out, by carrying out the complete emptying of the cannulated body 2 up to its proximal end 4.

Thanks to the device 1 of the present invention optimal delivery conditions are ensured even of fluid and/or granular material.

Moreover, thanks to the dimensions of the device 1, the operator actuates the device 1 from a safety distance, necessary so as not to be subjected to too much radiation.

The cannulated body 2 has dimensions and materials that are selected so as to give the device 1 itself a good rigidity. In this way, it is made easier to correctly deliver and arrange the biocompatible material in the anatomical injection site, preventing the end section 6 being able to accidentally straighten or change angle of inclination under the action of the forces that deliver the material itself.

Moreover, thanks to the fact that it is integral and rigid, the cannulated body 2 does not risk losing the direction of curvature or of varying it during use, ensuring the delivery of the material to the desired site.

In particular, the cannulated body 2 of the injector device 1 is rigid and is made from a rigid material; once it is made, it has a configuration that cannot be modified or deformed any more by the user. The material with which the cannulated body 2 is made comprises a biocompatible metal, such as titanium, steel, AISI 316, etc., or a neutral or radiopaque plastic resin, or a material suitable for the purpose or a mixture thereof.

The injector device 1 also comprises a piston 7 connected to a shaft 8.

The piston 7 is made from radiopaque material, so that, during injection, it is always possible to view, through routine viewing techniques, the exact point at which the piston 7 is located.

The piston 7 has a diameter corresponding to the internal diameter of the cannulated body 2 and of the inner lumen 5 in order to ensure a hermetic seal between the piston itself and the cannulated body 2.

Figure 5:
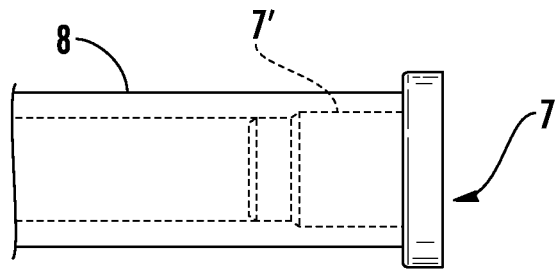
FIG. 5 is an enlarged side view of a detail of the component of FIG. 4.
Figure 6:
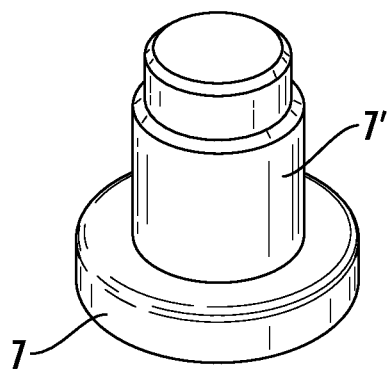
FIG. 6 is a perspective view of an element of the component according to FIGS. 4 and 5.

The piston 7, as can be seen in FIGS. 5 and 6, is substantially shaped like a plug and is equipped with a stem 7'.

Such a stem 7' can be inserted through a threading, or a snap-coupling, or another known technique, into the shaft 8. The shaft 8 is therefore internally hollow or hollow at least at an end thereof in contact with the piston 7.

In a version of the invention, both the piston 7 and the stem 7' are made from radiopaque material, so that during injection it is always possible to view, through routine viewing techniques, their exact position.

The shaft 8 of the piston 7 has a smaller diameter than that of the piston 7 or of the inner lumen 5 of the cannulated body 2.

The shaft 8 of the piston 7 is graduated, so as to dose the amount of material inserted into the injector device 1 and thereafter the amount of material extruded.

The material from which the piston 7 and/or the shaft 8 and/or the stem 7' is made comprises a biocompatible metal, such as titanium, steel, AISI 316, etc., or a neutral or radiopaque plastic resin, or a material suitable for the purpose or a mixture thereof.

However, since the shaft 8 must be able to flex, as will become clearer hereafter, the material of the shaft 8 is softer than that of the piston 7 or of the stem 7' or of the cannulated body 2.

In particular, the material from which the shaft 8 is made is a soft plastic resin or a flexible metal or a sheet of harmonic steel, in other words a material that is flexible but still able to withstand the necessary pressure exerted for delivery.

The shaft 8 has a rectilinear but flexible configuration. Therefore, the shaft 8, while the piston 7 pushes the material, flexes and is able to follow the path of the cannulated body 2, even in its end section 6 that is curved and/or bent.

The delivery mouth 40 can be made from radiopaque material, in order to view its position during delivery, and thus control the exact injection site.

The cannulated body 2 can have, in an embodiment of the invention, an element, for example annular in shape, at its proximal end 4. Also in this way, it is possible to make the delivery mouth of the cannulated body 2 itself visible. The material can be made radiopaque by adding barium and/or tungsten and/or tantalum sulphate and/or other suitable materials to the base material.

The radiopaqueness can have various degrees of opaqueness to X-rays. Therefore, it is possible to make a piston 7 that is very radiopaque and a cannulated body 2 having slight radiopaqueness. Moreover, it is possible to add radiopaque substances also to the material to be extruded. In this case, it will be possible to control the insertion of the cannulated body 2, possibly follow the positioning of its extrusion mouth 40 thanks to the radiopaque element positioned at it, and see and distinguish both the piston 7 that advances, and the material that is extruded.

Moreover, the radiopaqueness is additional: in other words the areas of juxtaposition between two radiopaque materials are more radiopaque than the starting materials, with the possibility of making it possible to see a radiopaque material sliding inside a further radiopaque material.

The end section 6 that is curved and/or bent of the cannulated body 2 has some critical features. Indeed, maintaining its curvature and/or its bend proved critical over time.

In a version of the invention, the end section 6 of the cannulated body 2 is made by deformation and/or hot-bending of the cannulated body, initially made in straight configuration. Such a deformation and/or bending step takes place at about 160° C. for a variable time of between 6 and 12 hours and in the absence of humidity.

In particular, in order to prevent the cannulated body 2 from deforming in an undesired manner or from squashing making its internal diameter vary or other, such a deformation and/or bending step takes place using a template or a metallic shape and stainless steel pins, inserted inside the cannulated body 2, in order to maintain its curvature and/or bend in the end section 6 and its internal diameter.

In this way, the end section 6 of the cannulated body 2 keeps its curvature and/or bend unchanged over time and also following a test heating to 60° C. for a time period of three days. Therefore, the end section (6) is undeformable.

The injector device 1 also has handgrip means 12, connected to the distal end 3 of the cannulated body 2.

Moreover, at the end of the shaft 8 opposite the piston 7 there are further handgrip means 13, corresponding and complementary to the handgrip means 12 positioned on the cannulated body 2.

In this way, the holding, gripping and force to be applied onto the piston are secure and easy for the user. Moreover, the injector device 1 contains the biocompatible material to be injected.

The loading of the injector device 1 takes place through the proximal end 4 thereof. Such loading takes place through at least one immersion of the injector device 1, in particular of its proximal end 4, in a container containing such a material. Due to the viscous and/or granular nature of the biocompatible material, its loading inside the injector device 1 is very arduous.

In order to avoid this drawback, the proximal end 4, the extrusion mouth 40 and the cannulated body 2 have predetermined dimensions.

In particular, the cannulated body 2 has an internal diameter, which corresponds to the diameter of the inner lumen 5, not less than 7.5 mm in the case of corpuscular biological material.

Such a diameter, in a version of the invention, corresponds to a volume of at least 1.5 ml of biological material.

In a version of the invention, the cannulated body 2 has an internal diameter that corresponds to the diameter of the inner lumen 5, up to 5 mm in the case of biocompatible material in fluid or gel form but without corpuscles or having small sized corpuscles.

The extrusion mouth, in a version of the invention, can have a different diameter from that of the rectilinear portion 9 or of the end section 6 of the cannulated body 2, for example in cases in which it is necessary to have a widened section for outlet or inlet of the material during loading of the device 1.

Optionally, there can be reducing means to be applied to the extrusion mouth 40 for those situations in which the diameter thereof must be reduced.

Indeed, the fact of obtaining easy loading of the biocompatible material depends on the dimensions of the granules and on the dimensions of the proximal end 4 and of the extrusion mouth 40 of the device itself.

In a version of the invention, in order to ensure the correct rigidity of the cannulated body 2, its outer diameter is 9.5 mm or 10 mm.

In a further version of the invention, the thickness of the wall of the cannulated body 2 has a size comprised between 1 mm and 2.5 mm.

The dimensions of the cannulated body 2 of the injector device 1 are decisive for its function and not mere production choices. Indeed, considering that the material to be extruded can have granules of dimensions up to 5 mm or of also other dimensions, the internal diameter of such a cannulated body 2 must have specific dimensions in order to ensure correct delivery of the material, homogeneous filling of the device 1 and a rigidity such as to prevent the end section 6 being able to undergo changes in orientation or inclination, due to the delivery pressure, with the danger of delivering the material to a location that is not wanted or even not suitable for receiving such a material.

It has thus been seen how the invention achieves the proposed purposes.

In particular, the injector device 1 according to the present invention is substantially a monoblock and predetermined. Therefore, it is extremely easy to use, without the need to assemble and disassemble its components during the injection of the biological material. In this way, the operating time is reduced, with lower risks and discomfort for the patient.

Moreover, the loading of the injector device 1 is extremely simplified, even in the presence of biological material comprising granules of substantial dimensions or that are particularly viscous.

Finally, thanks to the length of the injector device 1 and the presence of the piston 7 possibly made from radiopaque material, the extrusion of the material can be controlled and actuated by the operator located a considerable distance from the patient, with lower risk of exposure to the rays or radiation to which the patient is subjected during the operation.

The present invention has been described according to preferred embodiments, but equivalent variants can be conceived without departing from the scope of protection offered by the following claims.

The invention claimed is:

1. An injector device for introducing biocompatible material into deep anatomical areas, positioned at the spine, the pelvis, the rachis and other similar locations, comprising:
    a cannulated body;
    a piston for delivering said biocompatible material, the piston being equipped with a shaft, wherein said cannulated body has a distal end, facing towards a user, and a proximal end, facing towards said anatomical area;
    wherein said cannulated body is monolithic and comprises a rectilinear section, equipped with a longitudinal axis, an inner lumen, and an end section that is curved and/or bent at said proximal end,
    wherein said proximal end comprises an extrusion mouth of said cannula for extruding biocompatible material, wherein said extrusion mouth, said end section and said rectilinear section are comprised of a single continuous piece and wherein the extrusion mouth is wider than at least one of the rectilinear section or of the end section,
    wherein said cannulated body is made from a rigid material, and said shaft has a rectilinear and flexible configuration so as to follow the path of said cannulated body, including in its end section that is curved and/or bent.

2. The device according to claim 1, wherein said end section has a predetermined angle of curvature of said end section that is curved and/or bent with respect to said longitudinal axis of said rectilinear section.

3. The device according to claim 2, wherein said predetermined angle of curvature, of said end section that is curved and/or bent with respect to said longitudinal axis of said rectilinear section, is comprised between 0° and 90° or between 5° and 70° or between 15° and 45° or it is 30°.

4. The device according to claim 1, wherein said shaft is rectilinear and flexible and it is made from a strong and flexible material including at least one of a soft plastic resin, a flexible biocompatible metal or a sheet of harmonic steel or from any material suitable for bending to follow the configuration of said cannulated body and suitable for withstanding a delivery pressure acting on said piston, wherein said material is neutral or radiopaque.

5. The device according to claim 1, wherein said cannulated body comprises, at its proximal end or the extrusion mouth, an element or a ring made from radiopaque material.

6. The device according to claim 1, wherein said cannulated body and/or said piston is made from a neutral or radiopaque material, biocompatible metal, titanium, steel, AISI 316, or from a neutral or radiopaque plastic resin, or a material suitable for the purpose or a mixture thereof.

7. The device according to claim 6, wherein said radiopaque material contains barium, tungsten, tantalum, or a substance suitable for the purpose or a mixture thereof.

8. The device according to claim 1, wherein said end section that is curved and/or bent is positioned between said extrusion mouth and said rectilinear section of said cannulated body.

9. The device according to claim 1, wherein said biocompatible material comprises osteoinductive material, biological material, bone paste, bone material, bone substitute material, bone substitutes in general, demineralized bone matrix, synthetic bone material, synthetic biological adduct, bone cement, material comprising particles or granules of demineralized bone or of synthetic granular material, mixtures thereof and similar materials suitable for the purpose, wherein said biocompatible material is neutral or radiopaque.

10. The device according to claim 1, wherein said biocompatible material has a pasty and/or gel-like and/or viscous consistency.

11. The device according to claim 9, wherein said particles or granules have dimensions of up to 15 mm or comprised between 1 mm and 5 mm.

12. The device according to claim 1, wherein said cannulated body has an internal diameter of more than 7.5 mm.

13. The device according to claim 1, wherein said cannulated body has an internal diameter of less than 7.5 mm.

14. The device according to claim 1, wherein said cannulated body has an outer tubular wall of thickness comprised between 1 mm and 2.5 mm and/or an outer diameter comprised between 9.5 mm and 10 mm.

15. The device according to claim 1, wherein said shaft of said piston is graduated.

16. The device according to claim 1, wherein said piston has a stem suitable for inserting in said shaft, wherein said shaft is hollow at least at its end in contact with said piston.

17. The device according to claim 1, further comprising handgrip means, connected to said distal end of said cannulated body and/or handgrip means, connected to said shaft in an end thereof opposite said piston.

* * * * *